United States Patent [19]

Kalbacher et al.

[11] 4,440,692

[45] Apr. 3, 1984

[54] SUBSTITUTED CARBONIC ACID ESTERS

[76] Inventors: Hubert Kalbacher, Hefelestrasse 15, 7407 Rottenburg/Neckar; Wolfgang Voelter, Panoramastrasse 71, 7400 Tuebingen-Hagelloch, both of Fed. Rep. of Germany

[21] Appl. No.: 372,798

[22] Filed: Apr. 28, 1982

Related U.S. Application Data

[63] Continuation of Ser. No. 71,668, Aug. 31, 1979, abandoned.

[51] Int. Cl.³ .................. C07C 69/96; C07C 125/063
[52] U.S. Cl. ............................. 260/463; 260/112.5 R; 260/349; 560/32; 560/162; 548/528
[58] Field of Search ................. 260/463, 349; 548/528

[56] References Cited

U.S. PATENT DOCUMENTS 3,705,213  12/1972  Pfeiffer et al. ..................... 260/463

FOREIGN PATENT DOCUMENTS 10587    5/1980  European Pat. Off. ............ 260/463
1106272  3/1968  United Kingdom .

Primary Examiner—Anton H. Sutto
Attorney, Agent, or Firm—Birch, Stewart, Kolasch & Birch

[57] ABSTRACT

Substituted carbonic acid esters and urethanes having the formula

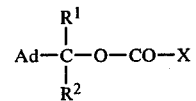

wherein Ad is a substituted or unsubstituted 1-adamantyl residue, $R^1$ and $R^2$ are saturated alkyl groups and X is chlorine, fluorine, azido or unsubstituted or substituted phenoxy. These compounds can be used in the synthesis of various peptides.

7 Claims, No Drawings

SUBSTITUTED CARBONIC ACID ESTERS

This application is a continuation of copending application Ser. No. 071,668, filed on Aug. 31, 1979, now abandoned.

BACKGROUND OF THE INVENTION

The present invention relates to novel substituted carbonic acid esters and urethanes, processes for their preparation, and the use thereof.

Numerous blocking groups are known for use in the reaction of primary and secondary amines, especially amino acids, biogenic amines, and amino sugars. A more recent compilatory disclosure is found, for example, in the two books by W. Wünsch and E. Müller (Editor), Houben-Weyl, "Methoden der Organischen Chemie" (Methods of Organic Chemistry), 15/1, Georg Thieme publishers, Stuttgart, 1974, and H. D. Jakubke and H. Jeschkeit, "Aminosäuren-Peptide-Proteine" (Amino Acids-Peptides-Proteins), 2nd Edition, Adademie Publishers, Berlin 1973.

Although the conventional amino blocking groups of the urethane type (Boc, Z) accomplished many of the requirements of unequivocally progressing structural synthesis principles, it is desirable in many instances to employ blocking groups which can be split off under very gentle acidolytic conditions. This permits an optimally gentle treatment of acid-labile blocking groups, for example, on trifunctional amino acids, and especially, for instance, in syntheses with repetitive coupling and unblocking steps (solid-phase or liquid-phase techniques). Also, tryptophancontaining peptides, for example, frequently experience a destruction of the indole system during deacylations in a more strongly acidic medium, manifesting itself in a violet discoloration and a shift in UV absorption. Secondary reactions of this type can be reduced to a minimum when using gentle unblocking reagents.

The following abbreviations are used throughout this application for convenience: Boc=tert-butoxycarbonyl; Bzl=benzyl; Z=benzyloxycarbonyl; DCC=dicyclohexylcarbodiimide; DCHA=dicyclohexylamine; DMF=dimethylformamide; HOBt=1-hydroxybenzotriazole; HoSu=N-hydroxysuccinimide; Ph=phenyl; "Triton B"=trimethylbenzylammonium hydroxide.

The recently developed blocking groups Bpoc, Ddz, Ppoc, Azoc (abbreviations in accordance with the general rules of peptide chemistry, cf. Houben-Weyl, "Methoden der Organischen Chemie," 15/1, Georg Thieme publishers, Stuttgart, 1974 and H. D. Jakubke and H. Jeschkeit, "Aminosäuren-Peptide-Proteine," 2nd Edition, Akademie publishers, Berlin, 1973), meet these requirements, but only the first two compounds are suitable for more widespread use. In both cases, the storage of the blocked amino acids is not entirely without problems for reasons of autocatalytical decomposition and/or photoability. Also the Bpoc phenyl carbonate, frequently employed for introducing the Bpoc group, tends to decompose even at low temperatures. The production of Bpoc-Trp-OH is accomplished only with very low yields.

SUMMARY OF THE INVENTION

In accordance with the present invention, it has now been surprisingly found that it is possible with the aid of the compounds of the invention as described below to introduce novel blocking groups for compounds with primary and secondary amino functions, especially amino acids, amino sugars, biogenic amines, exhibiting the following advantages over the prior art:

1. The introduction of the blocking group is achieved with the aid of stable, crystalline, and reactive compounds, such as phenyl carbonate (Adpoc-OPh) or fluorormic acid ester (Adpoc-F).
2. The Adpoc group can be removed under very gentle conditions. Blocking groups of the tert-butyl type remain unaffected. Tryptophan-containing peptides remain stable under the splitting-off conditions.
3. The blocking group is resistant to alkali as well as hydrogenolysis.
4. On the basis of its pronounced lipophilia, the Adpoc residue has strongly solubilizing properties, especially in the case of higher peptides.
5. Adpoc-Trp-OH can be prepared in high yields. The storage of these compounds under normal light conditions and at room temperature for three months did not result in any change of the derivative.
6. It is possible to utilize the methods customary in peptide chemistry (DCCI/HOBt active ester couplings, saponifications, hydrogenations), with the Adpoc residue remaining preserved.

The blocking group 2-adamantane-(1)-propyl-2-oxycarbonyl, called "Adpoc" hereinbelow, proves to be especially advantageous also due to the fact that the elimination of the N-[2-adamantane-(1)]-isopropyl blockage can be accomplished in a gentle acidolytic medium, namely preferably in 3% strength trifluoroacetic acid in methylene chloride within 4–5 minutes at 0° C. or within 2–3 minutes at room temperature. In this process, an extensive unblocking selectivity is attained with respect to blocking groups of the tert-butyl type. Of course, N-benzyloxycarbonyl, O-benzyl ether, as well as O-benzyl ester groupings remain intact.

The aforementioned cleavage conditions make it possible to split off this novel N-urethane blocking group more rapidly by a factor of $10^3$ as compared to the N-tert-butoxycarbonyl group. As constrasted to the N-[2-biphenyl-(4)]-oxycarbonyl-(Bpoc) blockage, however, Adpoc amino acids, under acidolytic conditions, exhibit approximately 2–3 times the stability of the former.

Therefore, this invention relates to compounds of general Formula I:

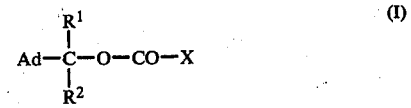

wherein,
Ad is the 1-adamantyl residue which can be substituted by alkyl groups (of 1–8 carbon atoms), alkoxy groups (of 1–8 carbon atoms), nitro groups, or halogen (fluorine, chlorine, bromine, iodine), or which can be unsubstituted, but which is preferably unsubstituted;
the residues $R^1$ and $R^2$ are saturated alkyl residues of 1–8 carbon atoms, preferably methyl groups; and
X is chlorine, fluorine, azido, phenoxy, which can optionally be substituted in the benzene nucleus by fluorine, chlorine, bromine, iodine, nitro, alkoxy groups, or alkyl groups, N-oxysuccinimido, or residues of the formulae

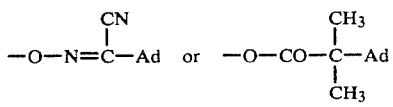

The novel compounds of general Formula I

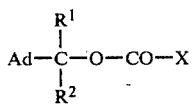

wherein Ad, $R^1$, $R^2$ and X have the meanings described above are prepared by reacting the corresponding 1-adamantanecarboxylic acid lower alkyl esters, preferably ethyl esters, with corresponding alkyl magnesium halides, preferably iodides, to obtain compounds of Formula II

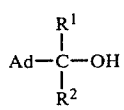

wherein Ad, $R^1$, and $R^2$ have the above-indicated meanings,
and by reacting these compounds with compounds of the general formula

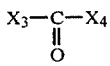

wherein $X_3$, $X_4$ are halogens (as defined above) or haloalkoxy groups.

The above-mentioned 1-adamantanecarboxylic acid esters are prepared from the acids in a manner known per se, for example, from the corresponding acids by treatment with suitable phosphorus halides and reaction with alcohols.

The term lower alkyl is understood to mean alkyl residues of from 1 to 8 carbon atoms.

The reaction schemes set forth below serve for explaining the process of this invention.

The invention relates furthermore to a process for the preparation of compounds of general Formula Ia:

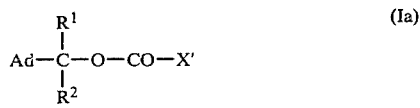

wherein,
Ad is the 1-adamantyl residue which can be substituted by alkyl groups (of 1–8 carbon atoms), alkoxy groups (of 1–8 carbon atoms), nitro groups, or halogen (fluorine, chlorine, bromine, iodine), or which can be unsubstituted, but which is preferably unsubstituted;
the residues $R^1$ and $R^2$ are saturated alkyl residues of 1–8 carbon atoms, preferably methyl groups; and
X' represents

residues of primary or secondary amino compounds, especially, however, D-, L-, or D,L-amino acids, biogenic amino sugars.

Amino acids are understood to mean organic compounds having a carboxy group and additionally possessing a —$NH_2$— or —NH—function, but especially glycine, alanine, leucine, isoleucine, serine, threonine, cysteine, cystine, methionine, proline, hydroxyproline, lysine, hydroxylysine, arginine, histidine, aspartic acid, asparagine, glutamic acid, glutamine, phenylalanine, tyrosine, and tryptophan. Biologically active amines are, in particular, tyramine, dopamine, noradrenalin, adrenalin, tryptamine, serotonin, melatonin, histamine, cysteamine, propanolamine, ethanolamine, cadaverine, putrescine, and agmatine. Amino sugars are understood to mean carbohydrates of a monomeric or polymeric kind, having a primary (—$NH_2$) or secondary (>NH—) function, e.g., glucosamine (2-amino-2-deoxyglucose) or galactosamine (2-amino-2-deoxygalactose).

The compounds of this invention are excellently suitable for peptide syntheses, especially for the synthesis of TRH, LH/FSH-RH, eledoisin, secretin, gastrin, physalemin, glucagon, adrenocorticotropin, oxytocin, vasopressin, and somatostatin. Another object of the inven-

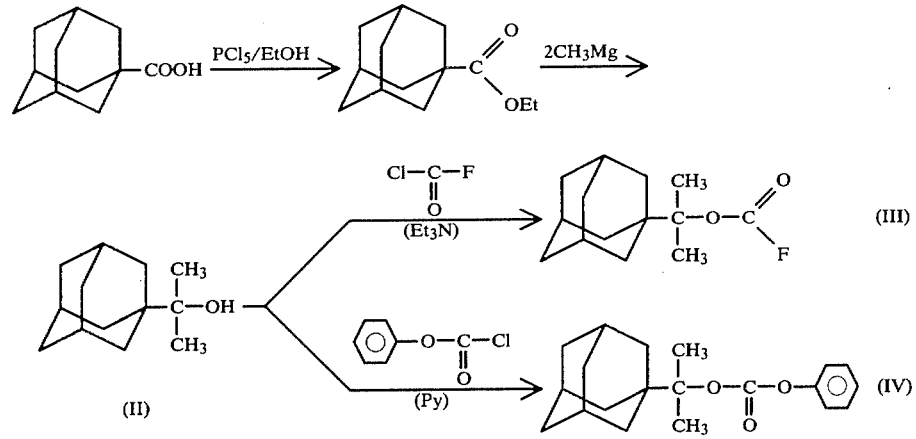

tion is therefore the use of the compounds in peptide syntheses, especially Adpoc-Gly-OH, Adpoc-L-Ala-DCHA, Adpoc-L-Gln-OH, Adpoc-L-Trp-OH, Adpoc-L-Trp-OSu, Adpoc-L-Trp-L-Lys(Z)-OH, Adpoc-L-Thr(Bzl)-OH, Adpoc-L-Thr(Bzl)-L-Phe-OCH$_3$, Adpoc-L-Thr(Bzl)-L-Phe-OH, Adpoc-L-Thr(Bzl)-L-Phe-L-Thr(Bzl)-L-Ser-(Bzl)-OCH$_3$, Adpoc-L-Trp-L-Lys(Z)-L-Thr(Bzl)-L-Phe-L-Thr(Bzl)-L-Ser-(OBzl)-OCH$_3$, as well as Adpoc-L-Trp-L-Lys(Z)-L-Thr(Bzl)-L-Phe-L-Thr(Bzl)-L-Ser-(OBzl)-L-Cys(Trt)-OH.

EXAMPLES OF THE INVENTION

The following examples are given merely as illustrative of the present invention and are not to be considered as limiting. Unless otherwise noted, the percentages therein are by weight.

The melting points were determined in the apparatus according to Dr. Tottoli and were not corrected. The specific rotation values were determined by a digital polarimeter OLD 5 from Zeiss. The thin-layer plates (instant TLC plates, silica gel 60F$_{254}$) were obtained from the Merck Company. Indicators: UV at 254 nm. ninhydrin and chlorotolidine reagent. The mobile phases employed for thin-layer chromatography were the following:

A: chloroform/methanol/benzene/H$_2$O (40:40:40:5)
B: butanol/glacial acetic acid/H$_2$O (3:1:1)
C: methanol/chloroform (2:1)

EXAMPLE 1

A. Fluoroformic Acid 2-Adamantyl-(1)-propyl-(2) Ester (Adpoc-F) (III).

During the course of 2–3 hours, dry, SO$_3$-free carbonyl chloride fluoride (obtained from 60 g. of 65% oleum and 25 ml. of fluorotrichloromethane) was directly incorporated at −40° C. by condensation into 19.4 g. (0.1 mole) of 2-adamantane-(1)-propanol-(2), prepared according to Tetrahedron 27: 3 (1971), in 150 ml. of dry ether and 14 ml. of triethylamine. During this step, triethylamine hydrochloride was precipitated. After the gas evolution had ceased, the mixture was allowed to stand overnight at −20° C.; then, the mixture was degasified at 200 Torr [mm. Hg] and 10° C. After filtration, the residue was additionally washed with dry ether on the filter. The filtrate contained 22.9 g. of Adpoc-F. This compound can be utilized in an ether solution or directly after concentration under vacuum. After removal of the solvent under vacuum, the fluoroformic acid ester can be obtained in crystalline form. In this reaction method, no carbinol can be detected any longer with the use of IR spectroscopy.

Melting point: 52° C.
IR: (KBr) 1815 cm$^{-1}$
Yield: 22.9 g. (95%)
C$_{14}$H$_{21}$O$_2$F (240.32)
Calculated: C 69.9, H 8.81, Found: C 70.25, H 8.99.

B. Preparation of the Adpoc Amino Acids 10 millimoles of the amino acid was dissolved under heating in 4.5 cc. of an approximately 40% solution of "Triton B" (benzyltrimethylammonium hydroxide) in methanol. The mixture was evaporated under vacuum, the residue was taken up in 5–10 cc. of dimethylformamide, whereupon the mixture was again evaporated and the process was repeated. The mixture was then dissolved in 10 cc. of dimethylformamide, cooled to −10° C., and combined at this temperature with 2.65 g. (11 millimoles) of Adpoc-F and 1.6 cc. of triethylamine. The mixture was agitated for 3 hours at −5° C., for 2 hours at 0° C., allowed to reach room temperature, and the reaction solution was then poured into 20 cc. of ice water. After extracting the mixture twice with, respectively, 20 ml. of ether-petroleum ether (1:1), the aqueous phase was acidified with citric acid and repeatedly extracted with, in total, 80 cc. of ether. The combined ether extracts were washed neutral with water; the ether was distilled off under vacuum after a brief drying over Na$_2$SO$_4$. The residue was made to crystallize either directly or after having been converted into the DCHA salt. The properties of the Adpoc amino acids prepared according to this method are listed in Table 1.

EXAMPLE 2

A. [2-Adamantane-(1)-propyl-(2)]-phenyl Carbonate (IV)

19.4 g. (0.1 mole) of 2-adamantane-(1)-propanol-(2), 100 ml. of dichloromethane, and 12.0 ml. of pyridine were combined at −5° C. within 30 minutes with a solution of 15.2 ml. of phenyl chloroformate in 50 ml. of dichloromethane. The precipitate formed during the dropwise addition was redissolved after stirring the mixture overnight at 0° C. The reaction mixture was poured on ice, diluted with 150 ml. of dichloromethane, and the organic phase was separated. After washing three times with water, the mixture was dried over sodium sulfate and evaporated under vacuum at 30° C. By recrystallizing twice from benzene/n-hexane, long, colorless crystals were obtained.

Melting point: 72° C.
Yield: 26.25 g. (83.5%),
C$_{20}$H$_{26}$O$_3$ (314.43).
Calculated: C 76.40, H 8.33, Found: C 76.55, H 8.43.

B. Preparation of the Adpoc Amino Acids 10 millimoles of the amino acid was dissolved under gentle heating in 4.6 cc. of an approximately 40% solution of "Triton B" (benzyltrimethylammonium hydroxide) in methanol. After evaporation of the solvent, the residue was freed of water by twice performing azeotropic distillation with, respectively, 30 ml. of dimethylformamide. The residue was taken up in 30 ml. of dimethylformamide at 50° C., combined with 3.8 g. (12 millimoles) of Adpoc-OPh, and the reaction mixture was agitated for 3 hours at 50° C. To work up the mixture, the latter was divided between water and diethyl ether-petroleum ether (1:1); the separated aqueous phase was acidified at 0° C. with 1 N citric acid solution (pH 2–3) and exhaustively extracted with diethyl ether. After the ether extracts were washed and dried in the usual manner, the mixture was evaporated to dryness uder vacuum. The remaining substance was made to crystallize ether directly or after conversion into the DCHA salt.

The properties of the Adpoc amino acids prepared in accordance with this process are indicated in Table 1.

TABLE 1

Preparation and Properties of Adpoc Amino Acids and Peptides*

| Amino Acid Derivative and Elementary Formula | Mol. Wt. | Yield % | M.P. (°C.) | $[\alpha]^{20}_D$ | Analysis Calculated Found C % | H % | N % | DC Rf$_4$ |
|---|---|---|---|---|---|---|---|---|
| Adpoc—Gly-13 OH $C_{16}H_{25}NO_4$ | 295.38 | 74 | 135° C. | — | 65.06 64.95 | 8.53 8.72 | 8.53 4.81 | 0.37 |
| Adpoc—Gly—DCHA $C_{28}H_{48}N_2O_4$ | 476.70 | | 158° C. | — | 70.54 70.69 | 10.15 10.20 | 5.88 5.89 | |
| Adpoc—Ala—DCHA $C_{29}H_{50}N_2O_4$ | 490.73 | 65 | 155° C. | +6.22° (c = 0.65, EtOH) | 70.98 71.20 | 10.27 10.17 | 5.70 5.79 | 0.45 |
| Adpoc—Gln—OH $C_{19}H_{30}N_2O_5$ | 366.46 | 61 | 98° C. | −2.96° (C= 0.8, EtOH) | 62.27 62.30 | 8.25 8.19 | 7.64 7.58 | 0.38 |
| Adpoc—Trp—OH $C_{25}H_{32}N_2O_4$ | 424.54 | 82 | 116° C. | −6.8° (c = 1.04 MeOH) | 70.73 | 7.60 | 6.60 | 0.48 |
| Adpoc—Trp—OSu $C_{29}H_{35}N_3O_6$ | 521.62 | 92 | 67–69° (decomp.) | −19.6 (c = 0.98, | 66.78 | 6.76 | 8.05 | 0.64 |
| Adpoc—Trp—Lys(Z)—OH $C_{39}H_{50}N_4O_7$ | 686.86 | 73 | 114–116° | −8.7° (c = 0.5 MeOH) | 68.20 69.32 | 7.33 7.45 | 8.16 7.97 | 0.47 |
| Adpoc—Thr(Bzl)—OH $C_{25}H_{35}NO_5$ | 429.56 | 69 | 50–52° | +19.8° (c = 10.2, MeOH) | 69.90 70.12 | 8.21 8.30 | 3.26 3.24 | |
| Adpoc—Thr(Bzl)—OH—DCHA $C_{37}H_{38}N_2O_5$ | 610.88 | | 130–131° | +12.9° (c = 1.03, MeOH) | 72.75 72.91 | 9.57 9.80 | 4.58 4.71 | 0.60 |
| Adpoc—Thr(Bzl)—Phe—OH $C_{34}H_{44}N_2O_6$ | 576.74 | 67 | 75–76° (decomp.) | −18.67° (c = 0.7, DMF) | 70.81 70.99 | 7.69 7.75 | 4.86 4.73 | 0.53 |
| Adpoc—Thr(Bzl)—Phe—Thr(Bzl)—Ser(Bzl)—OCH$_3$ $C_{56}H_{70}N_4O_{10}$ | 959.20 | 73 | 81° | +19.65° (c = 0.8, DMF) | 70.12 69.65 70.39 | 7.36 7.36 7.57 | 5.84 5.70 5.80 | 0.70 |
| Adpoc—Trp—Lys(Z)—Thr(Bzl)—Phe—Thr(Bzl)—Ser(Bzl)—OCH$_3$ $C_8H_{98}N_8O_{14}$ | 1407.73 | 68 | 164–165° | +11.7° (c = 0.5, DMF) | 69.11 69.29 | 7.01 7.11 | 7.96 8.04 | 0.73 |
| Adpoc—Trp—Lys(Z)—Thr(Bzl)—Phe—Thr(Bzl)—Ser(Bzl)—Cys(Trt)OH $C_{102}H_{115}N_9O_{15}S$ | 1739.12 | 82.4 | 150–152° | +8.6° (c = 0.45, DMF) | 70.44 70.31 | 6.66 6.58 | 7.24 7.36 | 0.76 |

*With the exception of glycine, the compounds are L-amino acid derivatives.

Preferred compounds in accordance with Formula (I) are the compounds

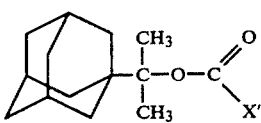

wherein X' is fluorine, chlorine, bromine, azido or phenoxy. These compounds can be prepared by reacting 1-adamantanecarboxylic acid with phosphorus pentachloride/ethanol and reacting the resulting product with methylmagnesium iodide (a Grignard reagent from methyl iodide and magnesium) to obtain 2-adamantane-(1)-propanol-(2) and CO(X')$_2$ wherein X' has the above-indicated meaning.

Alternative to the procedure described above for the preparation of the compounds having the general formula (I), these compounds can also be prepared by reacting the corresponding 1-adamantanecarboxylic acids by treatment with suitable phosphorus halides or thionyl chloride and reaction with alcohols to the 1-adamantane lower alkyl esters, preferably the ethyl esters, which are reacted with the corresponding alkyl magnesium halides, preferably the iodides, to give compounds having the following general formula (II):

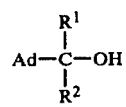

wherein Ad, $R^1$ and $R^2$ have the above-indicated meanings.

Other preferred novel compounds in accordance with the invention include:

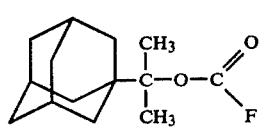

and

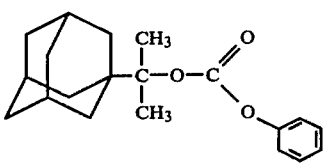

As noted above, the novel compounds of the invention can be employed to produce various peptides including, in addition to those enumerated above, calcitonin, angiotensin, bradikinin, callidin, phyllokinin, gramicidin, bacitracin, peptide antibiotics, peptide toxins, peptide insecticides, somatostatin, and respectively the partial sequences thereof. Such derivatives can be prepared by reacting the corresponding amino acids with the compounds of the invention and "Triton B". They also can be used for the preparation of various peptides such as tryptophan-containing peptides, as detailed above, as well as corticotropins, melanotropins, LH/FSH-RH, glucagon, calcitonins, gastrins, somatostatin and partial sequence thereof.

The invention being thus described, it will be obvious that the same may be varied in many ways. Such variations are not to be regarded as a departure from the spirit and scope of the invention, and all such modifications are intended to be included within the scope of the following claims.

What is claimed is:

1. Compounds having the formula:

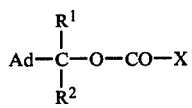

wherein,
Ad is the 1-adamantyl residue which is unsubstituted or substituted by alkyl groups of 1 to 8 carbon atoms, alkoxy groups of 1 to 8 carbon atoms, nitro groups, or halogen,
$R^1$ and $R^2$ are saturated alkyl groups of 1 to 8 carbon atoms; and
X is chlorine; fluorine; azido, phenoxy; phenoxy substituted in the benzene nucleus by fluorine, chlorine, bromine, iodine, nitro, alkoxy groups, or alkyl groups; N-oxysuccinimido; or residues having the formulae:

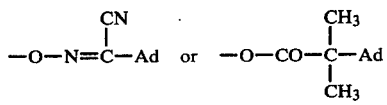

wherein Ad has the above-identified meaning.

2. The compounds according to claim 1, wherein $R^1$ and $R^2$ are methyl.

3. The compounds according to claim 1, wherein X is phenoxy substituted in the benzene nucleus by fluorine, chlorine, bromine, iodine, nitro, alkoxy groups, or alkyl groups; N-oxysuccinimido; or residues having the formulae:

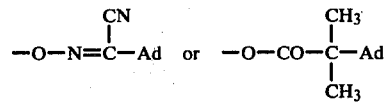

wherein Ad has the above-indicated meaning.

4. The compounds according to claim 1, wherein X is chlorine, fluorine, phenoxy; phenoxy substituted in the benzene nucleus by fluorine, chlorine, bromine, iodine, nitro, alkoxy or alkyl groups;

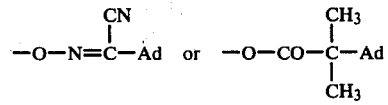

wherein Ad has the above-identified meaning.

5. The compounds accorrding to claim 4, of the formula:

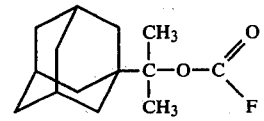

6. Compounds having the formula:

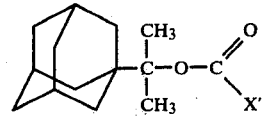

wherein X' represents fluorine, chlorine, bromine, azido or phenoxy.

7. The compound of the formula:

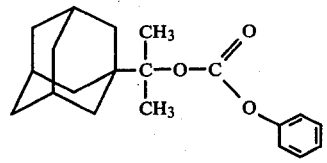

* * * * *

UNITED STATES PATENT AND TRADEMARK OFFICE
CERTIFICATE OF CORRECTION

PATENT NO. : 4,440,692
DATED : April 3, 1984
INVENTOR(S) : Kalbacher et al

It is certified that error appears in the above-identified patent and that said Letters Patent is hereby corrected as shown below:

In the Heading of the Patent, insert

--[30] Foreign Application Priority Data

Sep. 7, 1978 [LU] Luxembourg...........80,207--

Signed and Sealed this

Eleventh Day of December 1984

[SEAL]

Attest:

GERALD J. MOSSINGHOFF

*Attesting Officer*   *Commissioner of Patents and Trademarks*